(12) United States Patent
Varney

(10) Patent No.: US 7,990,277 B2
(45) Date of Patent: Aug. 2, 2011

(54) CALL CORD ALERT WITH BRACKET

(76) Inventor: Curtis R. Varney, Greeneville, TN (US)

( * ) Notice: Subject to any disclaimer, the term of this patent is extended or adjusted under 35 U.S.C. 154(b) by 174 days.

(21) Appl. No.: 12/262,571

(22) Filed: Oct. 31, 2008

(65) Prior Publication Data

US 2010/0109854 A1 May 6, 2010

(51) Int. Cl.
G08B 21/00 (2006.01)
(52) U.S. Cl. ..... 340/644; 340/664; 340/665; 340/573.1; 200/85 R
(58) Field of Classification Search ............ 340/644, 340/286.06, 286.07, 664, 665, 666, 573.1; 200/85 R
See application file for complete search history.

(56) References Cited

U.S. PATENT DOCUMENTS

| 4,067,005 | A | * | 1/1978 | Levy et al. | 340/573.4 |
| 4,179,692 | A | * | 12/1979 | Vance | 340/573.1 |
| 4,225,852 | A | * | 9/1980 | Waters et al. | 340/286.07 |
| 4,228,426 | A | * | 10/1980 | Roberts | 340/573.4 |
| 4,263,586 | A | * | 4/1981 | Nicholas | 200/85 R |
| 4,286,589 | A | * | 9/1981 | Thompson | 128/202.22 |
| 4,295,133 | A | * | 10/1981 | Vance | 340/573.4 |
| 4,770,377 | A | | 9/1988 | Callaway | |
| 5,137,033 | A | * | 8/1992 | Norton | 128/886 |
| 5,188,327 | A | | 2/1993 | White | |
| 5,614,887 | A | * | 3/1997 | Buchbinder | 340/573.1 |
| 5,963,137 | A | | 10/1999 | Waters, Sr. | |
| 6,917,293 | B2 | * | 7/2005 | Beggs | 340/573.1 |

* cited by examiner

Primary Examiner — Davetta W Goins
(74) Attorney, Agent, or Firm — Pitts, Lake & Bell, PC

(57) ABSTRACT

A call cord comprising an electrical wire or cable having one end thereof located at a nurse's station or other remote location to which it is desired to send an alert signal and a second end terminating proximate a medical patient or other user and including a push-button type switch. Intermediate the opposite ends of the call cord, there is provided a housed switch of the present invention whose actuation is a function of the physical engagement of the house switch within a operatively cooperative fixed mounting bracket for the housed switch. In the present invention, actuation of the housed switch may be accomplished as a function of the association or disassociation of the housed switch relative to the bracket.

12 Claims, 12 Drawing Sheets

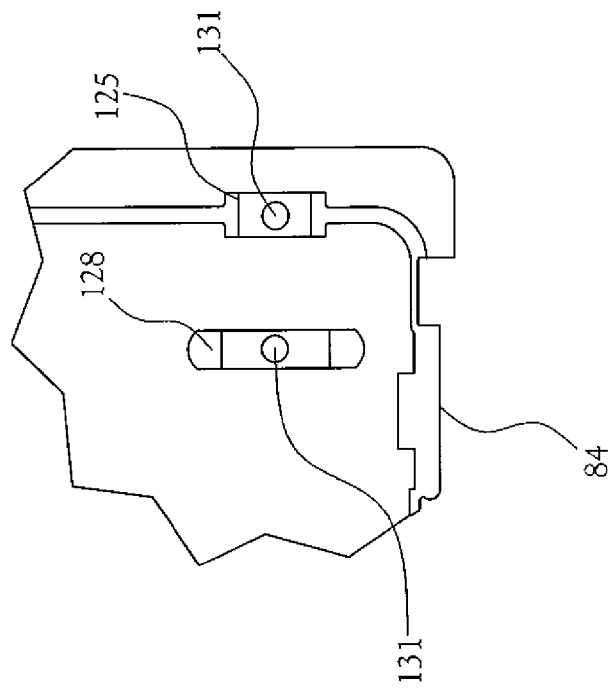
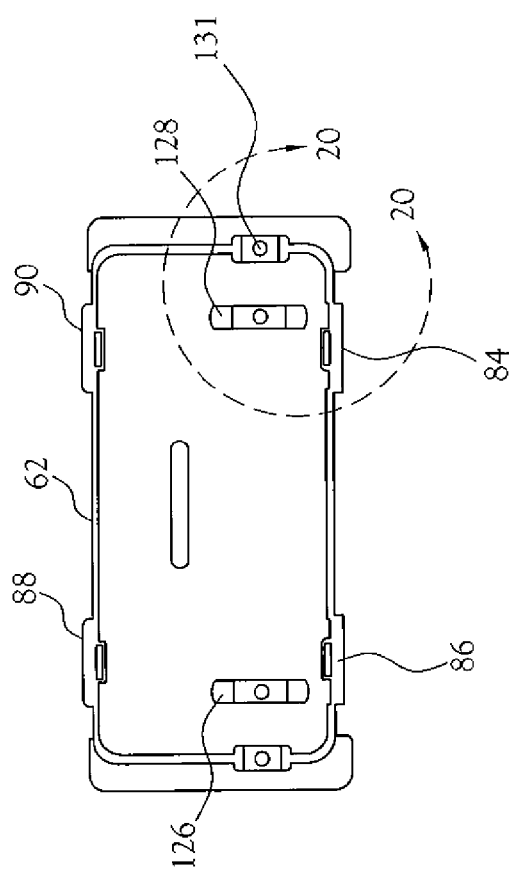
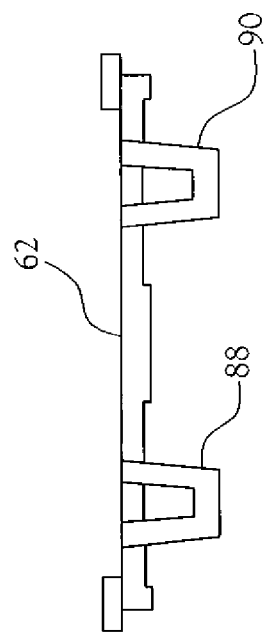

US 7,990,277 B2

CALL CORD ALERT WITH BRACKET

CROSS-REFERENCE TO RELATED APPLICATIONS

Not Applicable

STATEMENT REGARDING FEDERALLY SPONSORED RESEARCH OR DEVELOPMENT

Not Applicable

FIELD OF INVENTION

The present invention relates to devices useful for bedridden, or otherwise partially immobilized, especially medical, patients to signal for assistance employing an electrical call cord whose activation effects transmission of a signal from the patient to a care giver at a remote location.

BRIEF SUMMARY OF THE INVENTION

In medical treatment environments, it is common to provide a patient with means to signal from their bed or other location to a nurse or other care provider at a remote location, that assistance is needed. Herein, for clarity purposes, the "remote location" is referred to at times as a "nurse's station" 20

One common signaling device employs a call cord comprising an electrical cord leading from the location of the patient (normally in a bed) to a remote location, such as a nurse's station. The distal end of the call cord proximate the patient commonly is provided with a push button switch mounted in a hand held housing and adapted to open or close an electrical circuit, usually momentarily, when the button is pushed by the patient. This signal is received at the remote location as a buzzer, light, or other audible and/or visual means which alerts the caregiver to the need of assistance by the patient.

In similar manner, at times a care giver may be attending to a patient in a bed and occasion may arise for the care giver to need assistance with the patient. Under such circumstances, it is very desirable that the push-button-containing distal end of the call cord be readily available to the care giver so that help can be summoned quickly.

It is desired, therefore, that a call cord be "stored" in a location proximate a patient disposed in a bed, for example, and that such location be relatively permanently established such that the distal end of the call cord (and its push-button switch) and the patient, once having learned where the call cord is located on the bed, can easily locate such distal end of the call cord and activate the push-button switch to send an alert signal to a nurse's station or other chosen location.

Further, commonly call cords are connected to a terminal mounted on the wall of patient's room so that when the bed is moved about within the patient's room or is moved out of the room for any of various reasons, such as cleaning, transport of patient to a different location, etc. the call cord must necessarily be readily disassociated with the patient's bed for at least some period of time. Subsequently, when the bed is returned to its normal use attitude, re-association of the call cord with the bed and consequently positioning the call cord proximate the patient, is desired.

Moreover, under certain circumstances, disassociation of the call cord from the bed desirably is to be accomplished very quickly and freely, such as when the patient must be moved immediately and quickly to a treatment or operating room.

Importantly, in certain medical care environments, the patient may not have full control over all their faculties and may tend to activate the push-button switch repeatedly and unnecessarily, creating confusion within the nurse's station, and often resulting in unnecessary trips of a care giver from the station to the patient's room. It remains desirable that a care giver be able to use the push-button switch to send an alert signal seeking additional help with the patient, for example.

In any event, re-association of the call cord with the bed desirably positions the call cord at that location on the bed which it enjoyed prior to it being disassociated from the bed so that a patient or care giver can be assured that the call cord is readily available following the re-association of the call cord with the bed. At times, such consistency of location of the call cord relative to the bed, can prove to be critical such as when a night-time care giver is attending to a bed patient in partial darkness within the patient's room.

BRIEF DESCRIPTION OF FIGURES

FIG. 18 is a plan view of the inboard surface of the cover depicted in FIG. 17;

FIG. 19 is front end view of the cover depicted in FIG. 18;

FIG. 20 is a detail view of the right-hand corner of the base depicted in FIG. 19 and taken generally along the line 20-20 of FIG. 18.; and, FIG. 21 depicts one embodiment of an electrical circuit useful in the present invention.

DETAILED DESCRIPTION OF INVENTION

Figure 1:
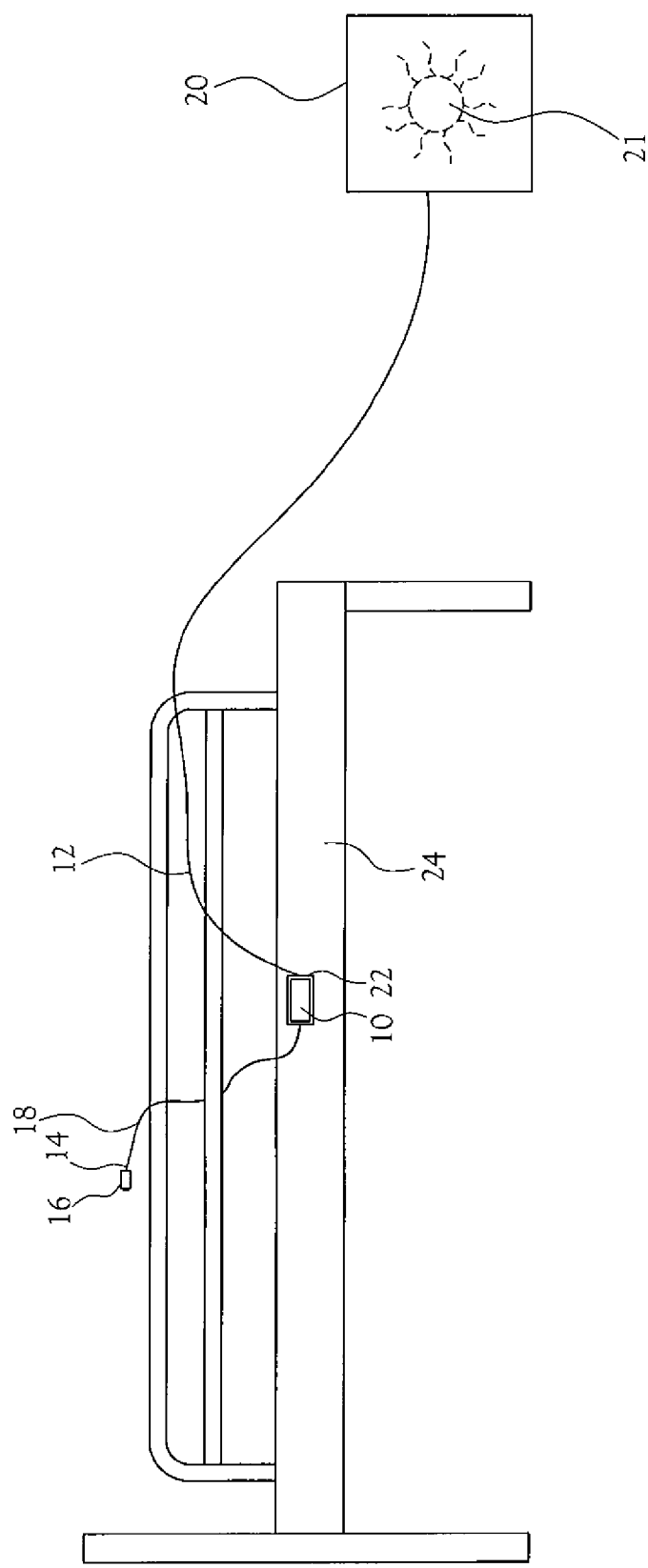
FIG. 1 is a schematic representation of a medical patient bed including a call cord and one embodiment of a switch housing of the present invention associated with the bed.
Figure 2:
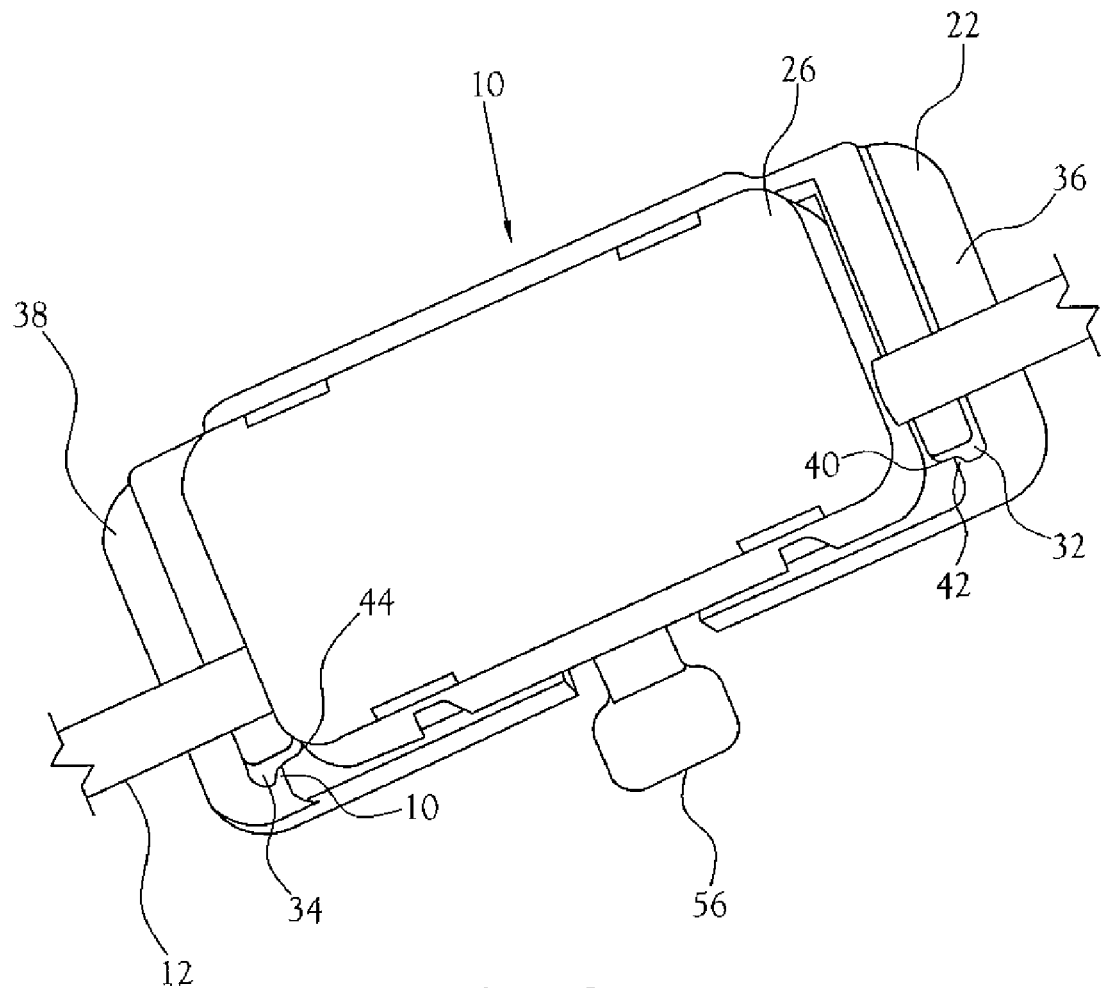
FIG. 2 is a representation of one embodiment of a bracket-mounted switch housing incorporated with a call cord of the present invention.

In the depicted embodiment of the present invention, a housed switch 10 is interposed along the length of a call cord 12, and preferably near the distal end 14 of the call cord and its push-button switch 16, but leaving a sufficient portion 18 of the length of the call cord freely moveable and of a length which discourages misplacement of the call cord, while also ensuring that the patient can readily capture the distal end of the call cord and actuate the push-button switch. In most instances, such distance is less than about thirty inches.

In accordance with one aspect of the present invention, the housed switch is incorporated into an electrical circuit (see FIG. 21) that includes the call cord and its push-button switch among other components. This housed switch may be a multiple pole type switch, such as a double pole, single throw switch. When actuated away from an initially biased state, the housed switch provides for electrical current flow to the push-button switch and thence to a nurse's station 20, when the push-button switch is activated, for initiating an alert signal 21, (commonly intermediate) such as a light and/or audible signal, at the nurse's station. Deactivation of the push-button switch, with simultaneous development of an alert signal (continuous) at the nurse's station is effected by actuation of the housed switch, towards the biased state, to redirect the electrical current flow through the circuit such that the electrical current flow to the push-button switch is rerouted through the housed switch direct to the nurse's station where an alert signal is generated. Such rerouting removes the push-button switch from communication with the circuit, therefore preventing normal use of the push-button switch to initiate an alert signal. However, the direct routing of the electrical current to the nurse' station continues to produce an alert signal within the nurse's station until such time as the housed switch is actuated away from an initially biased state to redirect the electrical flow to the push-button switch only. Actuation of the housed switch is effected in all instances by physical association or disassociation of the housed switch and the call cord relative to the bracket.

Provision is made in the present invention for easy and quick association and disassociation of the housed switch and the associated call cord relative to the bracket. In accordance with one aspect of the present invention, the location of the housed switch is established by affixing a bracket 22 to a stationary component, such as the bed frame 24 of the patient's bed, such bracket being adapted to releasably receive the housed switch and its associated call cord. In the depicted embodiment of the present invention, the association of the housed switch, which is interposed on the call cord, functions with the bracket to actuate the housed switch in the electrical circuit of the present invention and simultaneous directing of the electrical current to the push-button switch, thereby rendering the push-button switch operable for initiating an alert signal to the nurse's station. Disassociation of the housed switch and its associated call cord from the bracket actuates the switch to divert the electrical current away from the push-button switch and through the housed switch to initiate an alert signal to the nurse's station, rather than through the push-button switch.

As depicted, the housed switch, along with its associated portion of the call cord is mounted within a two-part switch housing 26 which is adapted to be manually releasably and operatively associated with the bracket which is affixed to a structural element of the bed or other fixed location, while locating the distal end of the call cord and its associated push-button switch readily accessibility to a patient and/or care giver.

One embodiment of the bracket of the present invention, as seen in FIGS. 3-10, may comprise a generally planar plate 28 which is adapted to be fixedly secured to a bed frame 24 or other structure of a patient's bed as by screws 94, 96 pop rivets or the like. Whereas there is depicted in the several Figures an open-face generally rectangular shaped bracket, it will be recognized that other geometry of the bracket may be chosen, but in any event, it is desirable that the bracket does not introduce an impediment to access to the patient reposed in the bed or by a care giver attending to the patient in the bed, for example.

Further, the bracket provides for the releasable acceptance of the housed switch and call cord in or on the bracket. To this end, in one embodiment of the present invention, an outboard face 29 of the bracket is adapted to be affixed to a bed structure or other suitable structure, and an inboard opposite face 30 of the bracket is exposed for acceptance of the housed switch in a manner which releasably joins the switch housing with the bracket. In the depicted embodiment, the outboard face of the bracket is provided with first and second elongated projections 32, 34 which extend along respective ones of first 36 and second 38 ends of the bracket. Each such projection extends perpendicularly away from the inboard face of the bracket and terminates in a distal planar edge 40,41 which extends in cantilevered fashion laterally inwardly of the bracket, thereby defining first and second open-ended channels 42, 44, respectively, along the opposite edges of the bracket. As will be noted, these channels serve to slidably receive therein respective elongated platforms 102, 104, defined on the opposite ends 46, 48 of the cover of the base of the switch housing Further, as seen in FIGS. 3-8, the bracket includes a rear wall 50 upstanding from the inboard face 30 of the bracket. Along the length of this wall there is provided a post 52 which projects from the rear wall in cantilevered fashion over the inboard face 30 of the bracket.

As will be seen hereinafter, this post functions to engage and actuate the housed switch disposed within the switch housing.

Figure 5:
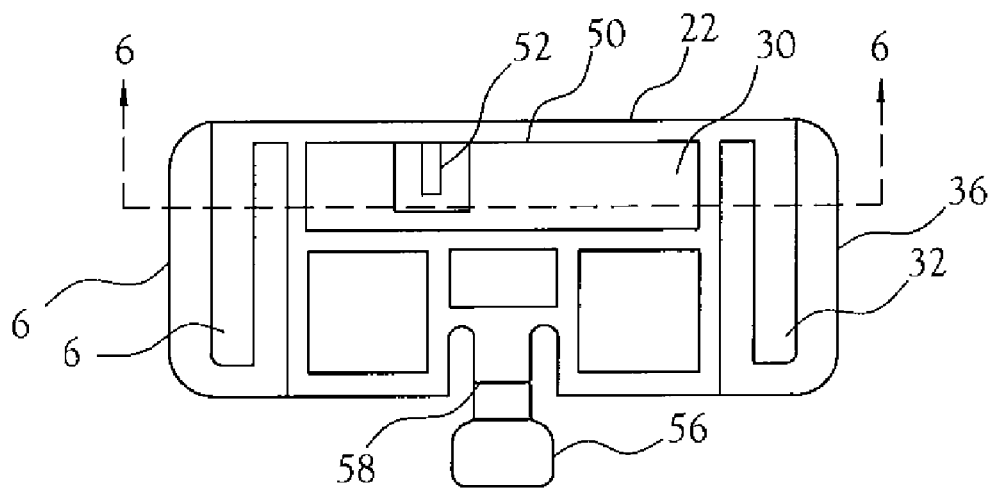
FIG. 5 is a plan view of the inboard side of the bracket depicted in FIG. 4.
Figure 6:
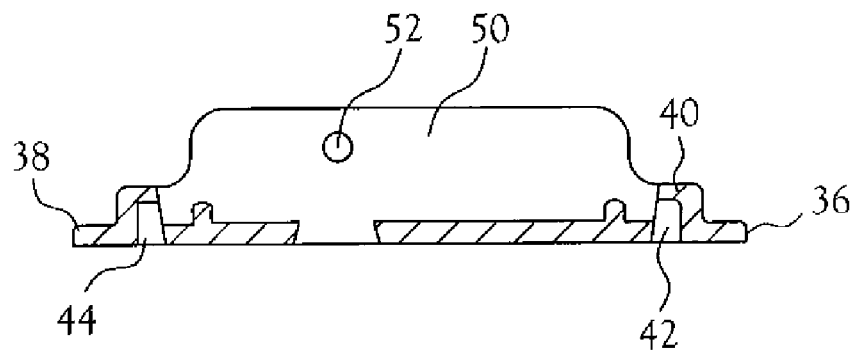
FIG. 6 is a sectional view of the bracket depicted in FIG. 6 and taken generally along line 6-6 of FIG. 5.
Figure 7:
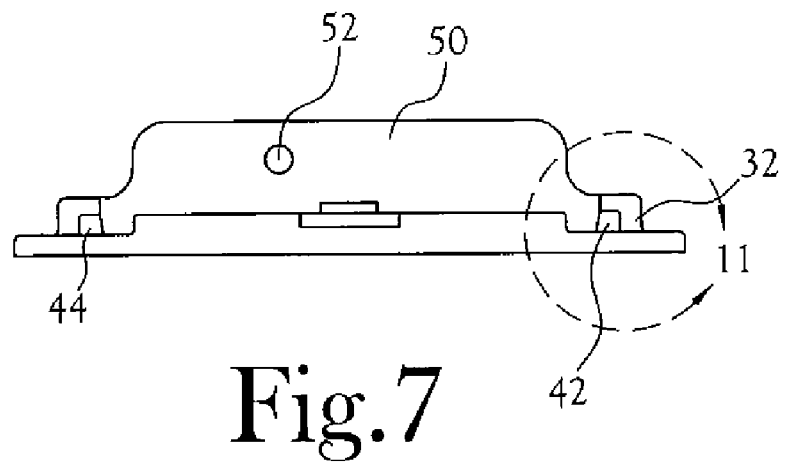
FIG. 7 is an end view of the bracket depicted in FIG. 5.
Figure 8:
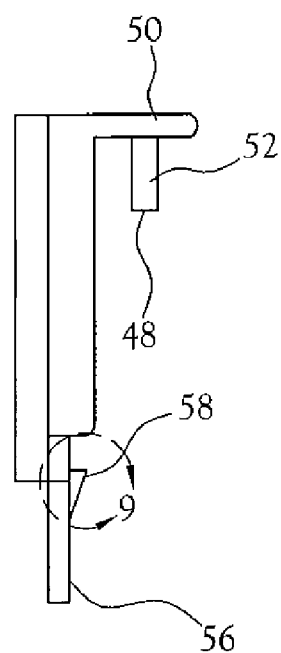
FIG. 8 a view of the left-hand end bracket depicted in FIG. 5 and depicting a latch associated with the bracket depicted in FIG. 6.
Figure 11:
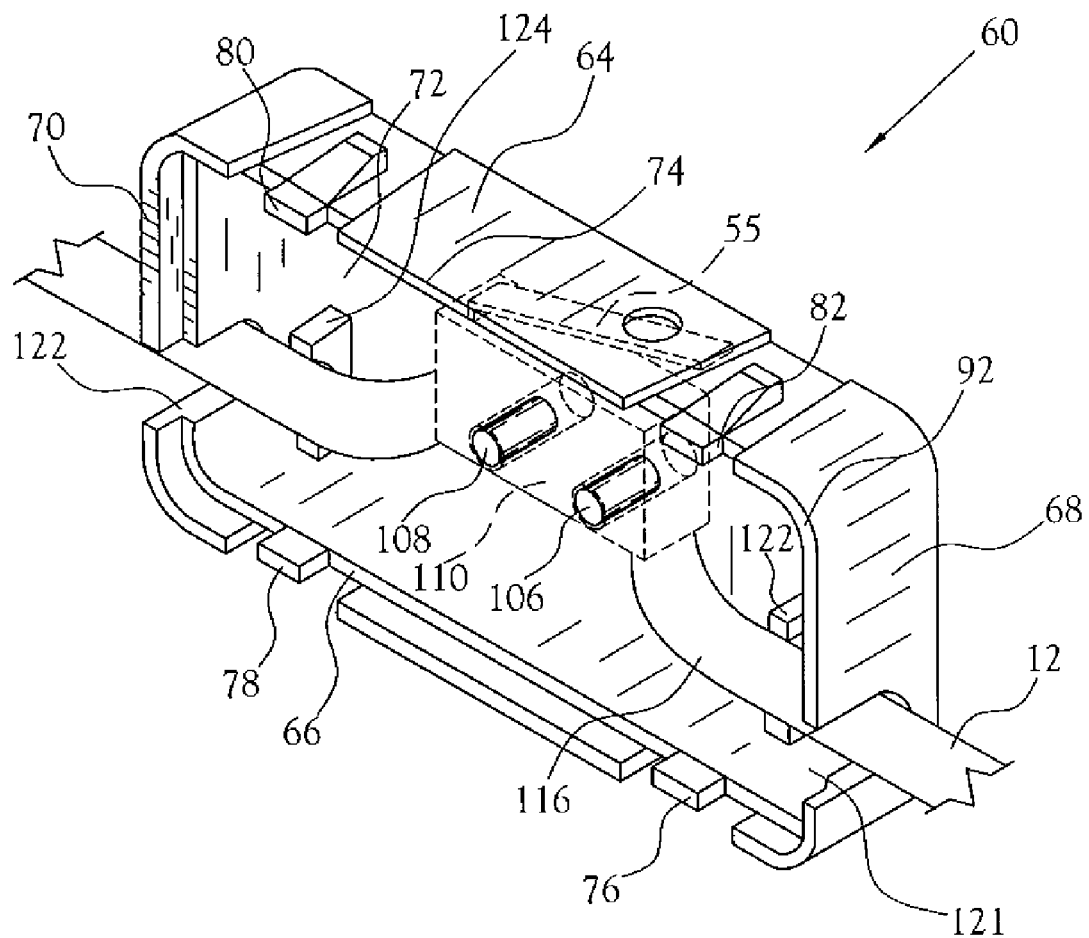
FIG. 11 is a representation of a base of a housing for a switch adapted to be interposed along the length of a call cord.

By design, as seen in FIGS. 5 and 11, the post 52 projecting from the inner wall of the top end of the bracket is chosen to be of a length such that, when the switch housing is fully inserted within the bracket, the outboard distal end 48 of this post will extend through an opening 53 in the wall of the base of the switch housing and into the interior of the housing to operatively engage the lever 55 of the housed switch and actuate the switch to place the push-button switch into communication with the electrical circuit (FIG. 21), thereby permitting actuation of the push-button switch to initiate an alert signal at the nurse's station. Contrariwise, when the housing becomes disassociated from the bracket, this post is withdrawn from engagement with the lever, and such lever, by reason of its internal bias, will actuate the housed switch to remove the push-button switch from communication with the electrical circuit and simultaneously divert the flow of electrical current direct to the alert device at the nurse's station. As noted, this switching action results in a "continuous" alert signal being displayed at the nurse's station so long as the switch housing is disassociated from the bracket. As noted, during the time period when the switch housing is disassociated from the bracket, the push-button switch is inoperative.

Figure 9:
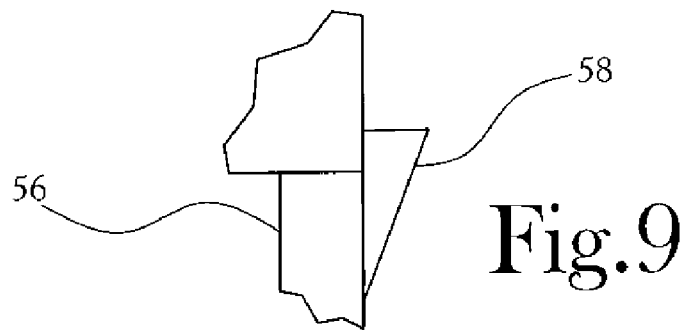
FIG. 9 is a detail side view of the latch depicted in FIG. 8.
Figure 10:
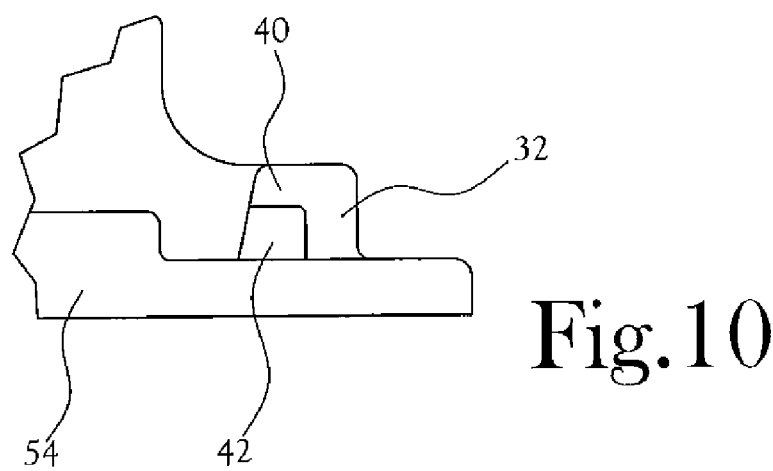
FIG. 10 is a detail view of the right-hand corner of the bracket depicted in FIG. 8 and taken generally along the line 11-11 of FIG. 7.

The front side 54 of the depicted bracket is provided with a latch 56 which in the depicted embodiment is formed of a flexible material, and which includes a catch 58 adapted to engage and releasably secure the switch housing within the bracket when such switch housing is received within the bracket. FIGS. 9 and 10 depict the latch in its relaxed state and in position to bend out of its plane when accepting the entry of the switch housing into the bracket and to rebound to engage and releasably lock the switch housing within the bracket when the switch housing is fully inserted within the bracket.

With reference to FIGS. 3 and 11-20, there is depicted one embodiment of a switch housing of the present invention, such switch housing comprising a base 60 of open-face rectangular box-like geometry. A generally planar plate defines a cover 62 for the base.

As seen in FIG. 11-16, the base of the switch housing includes a rear wall 64, a front wall 66 and first and second end walls 68, 70, respectively, each of which extends perpendicularly outwardly from the inboard face 72 of the base, thereby defining an interior chamber 74 for the base, such base having an outer peripheral rim 92. Within the rear wall and within the front wall of the base, there are provided first and second and third and fourth resilient snap fasteners 76, 78, 80 and 82, respectively, which are adapted to be received in mating first and second and third and fourth slotted resilient flaps 84, 86, 88 and 90, respectively, (FIGS. 17-19) which project from the rear wall and front wall of the cover at spaced apart locations along the length of such rear and front walls, and which are in register with the snap fasteners of the rear and front walls of the cover when the cover is affixed to the outer rim 92 of the walls of the base. Preferably, these snap fasteners and their mating slotted flaps are not amenable to disassociation from one another after they have once been fully joined to one another. This feature of the present switch housing precludes tampering with the electrical components disposed within the switch housing after the initial assembly of the housed switch and that portion of the call cord which is disposed within the switch housing.

In the depicted embodiment, the base of the housed switch is provided with open ended upstanding support mounts 122-124 and wall cutouts 121-122 for the call cord entering the housed switch. Mating support mounts 126,128 and cutouts 125,127 may be provided on the cover. Each of the support mounts and/or the cutouts may be provided with upstanding posts 131 (typical) designed to "bite" into the cord in a manner which ensures that the call cord is securely anchored against being pulled out of the switch housing during use.

Notably, the length of the cover 60 exceeds the length of its base 62 so that the opposite ends of the cover project beyond the ends of the base to define first and second elongated platforms 102 and 104, respectively, which are individually dimensioned to be slidably received within respective ones of the first and second channels 42, 44, defined at the opposite ends of the bracket. By this means, the assembled base and cover of this switch housing is slidably insertable into the bracket.

Figure 3:
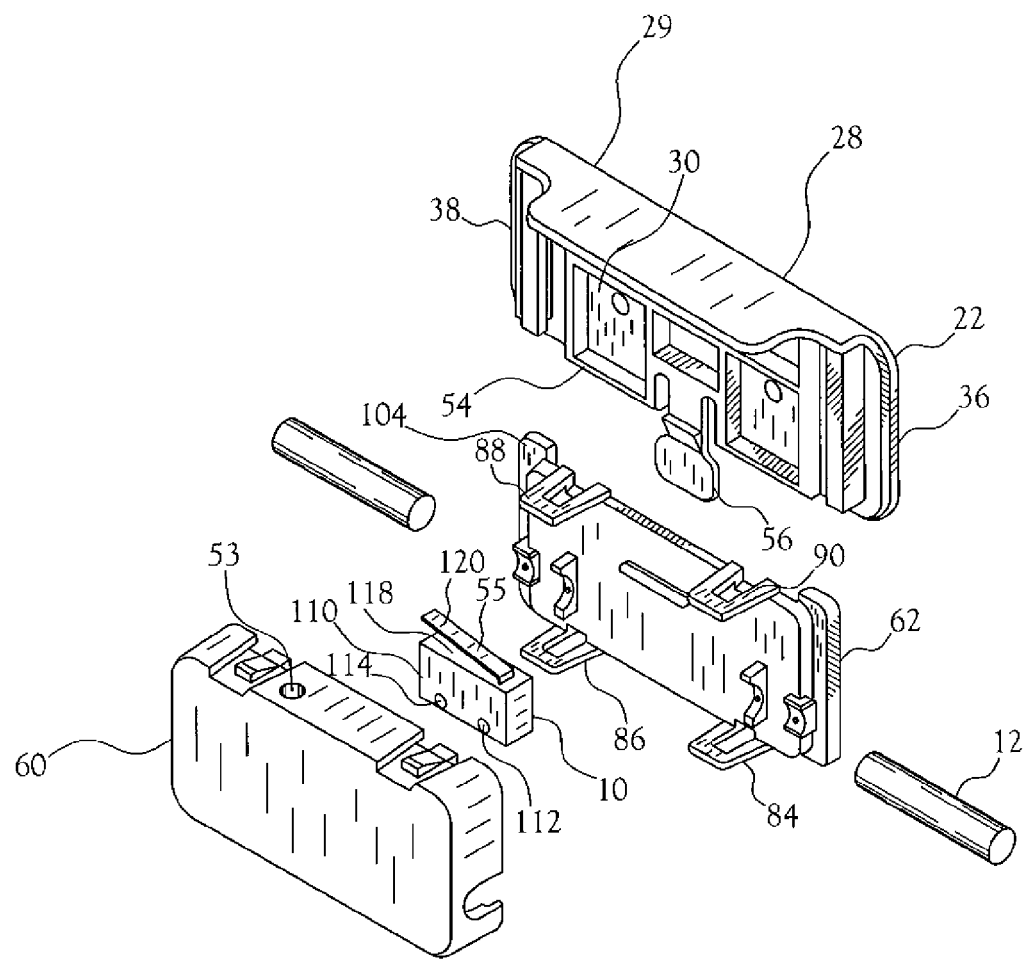
FIG. 3 is a partially exploded view of the bracket-mounted switch housing as depicted in FIG. 2.
Figure 4:
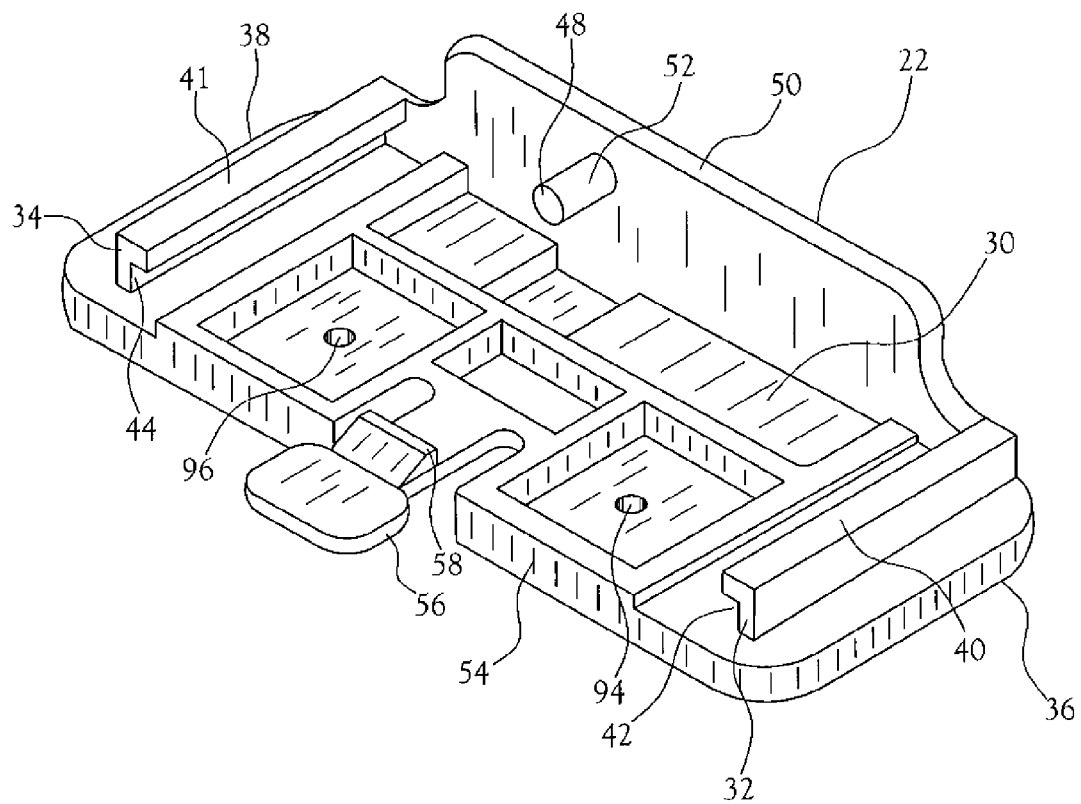
FIG. 4 is a perspective view of the inboard side of one embodiment of a bracket of the present invention.
Figure 12:
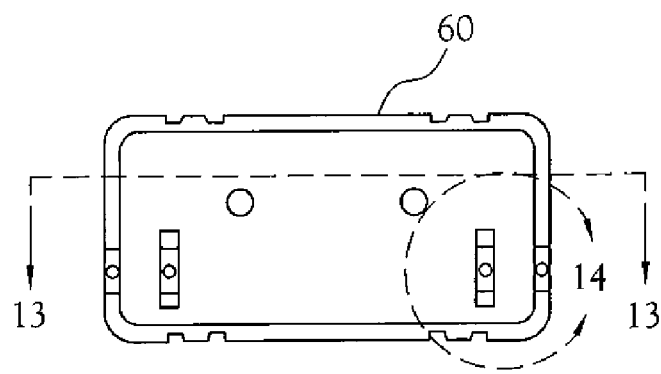
FIG. 12 is a plan view of the inboard surface of the base depicted in FIG. 11.
Figure 13:
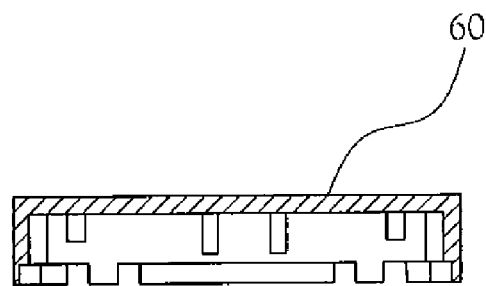
FIG. 13 is sectional view of the base depicted in FIG. 12 and taken generally along the line 13-13 of FIG. 12.
Figure 14:
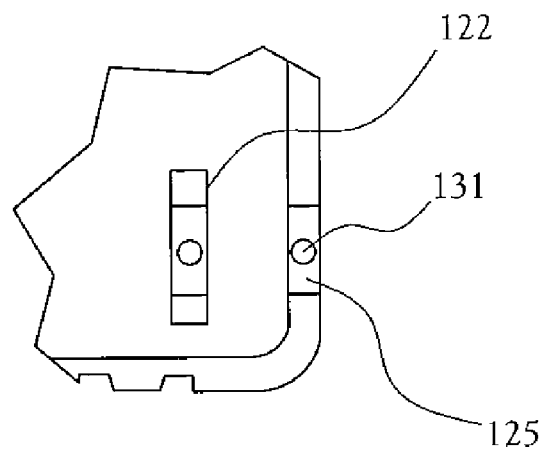
FIG. 14 is a detail view of a portion of a corner of the base depicted in FIG. 12 and taken generally along the line 14-14 of FIG. 12.
Figure 15:
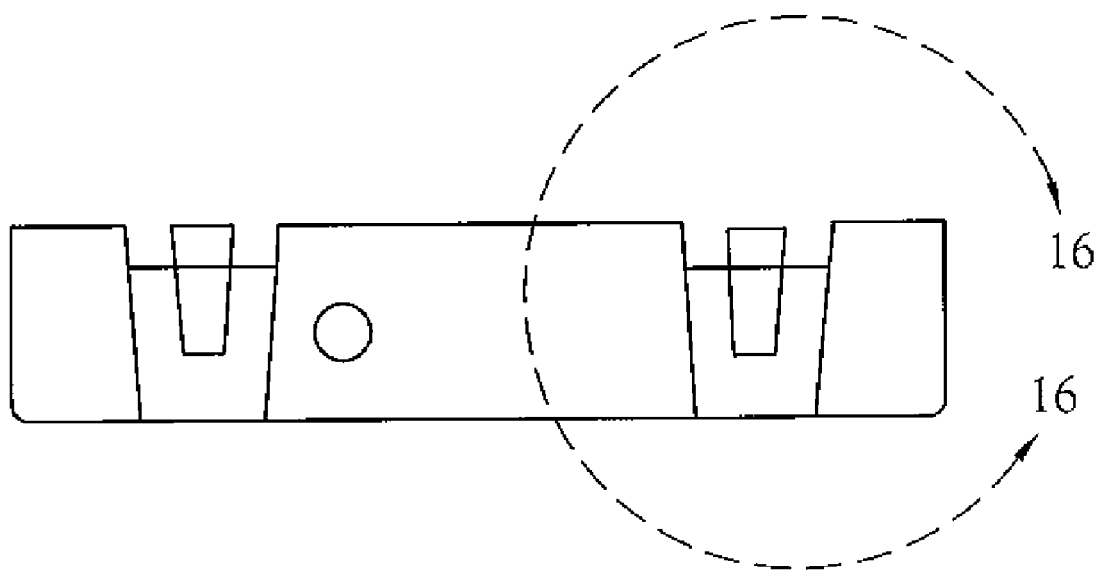
FIG. 15 is a front end view of the base depicted in FIG. 12.
Figure 16:
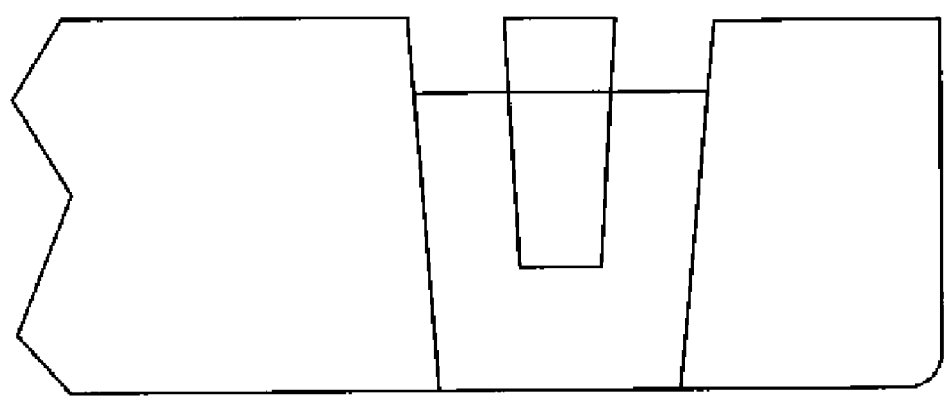
FIG. 16 is a detailed front view of the right-hand corner of the base depicted in FIG. 15.
Figure 17:
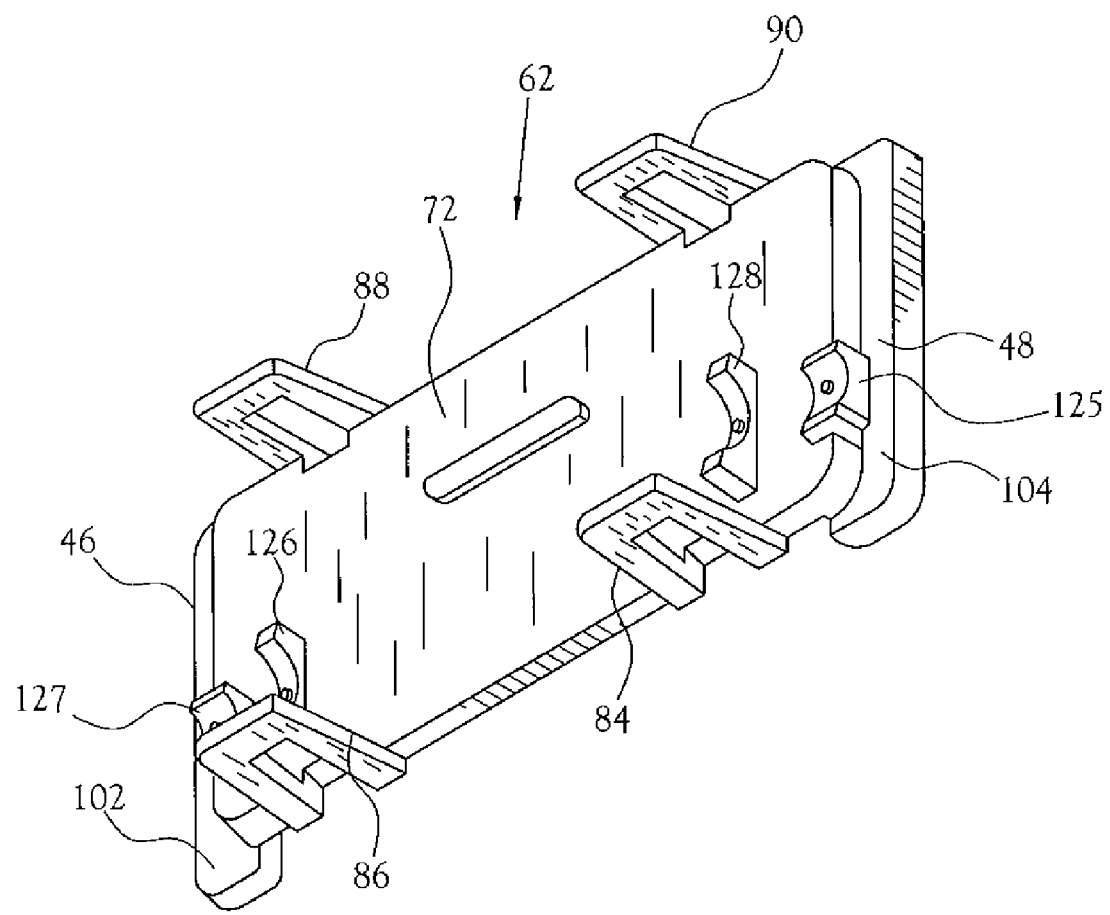
FIG. 17 is a representation of the inboard surface of a cover for the base depicted in FIG. 11.

Further, as depicted in FIG. 12, the base of the switch housing includes first and second posts 106 and 108 which project perpendicularly outward from the inboard face of the base. As seen in FIGS. 3 and 11, one acceptable housed switch for use in the present invention comprises a substantially rectangular body member 110 that is provided with first and second throughbores 112 and 114 extending into or through the thickness of the body member. As depicted in phantom in FIG. 11, mounting of the housed switch in the base in the depicted embodiment is effected by aligning these throughbores with the first and second posts which project from the inboard face of the base, and pushing the switch into overlying engagement with the inboard face of the base.

Figure 21:
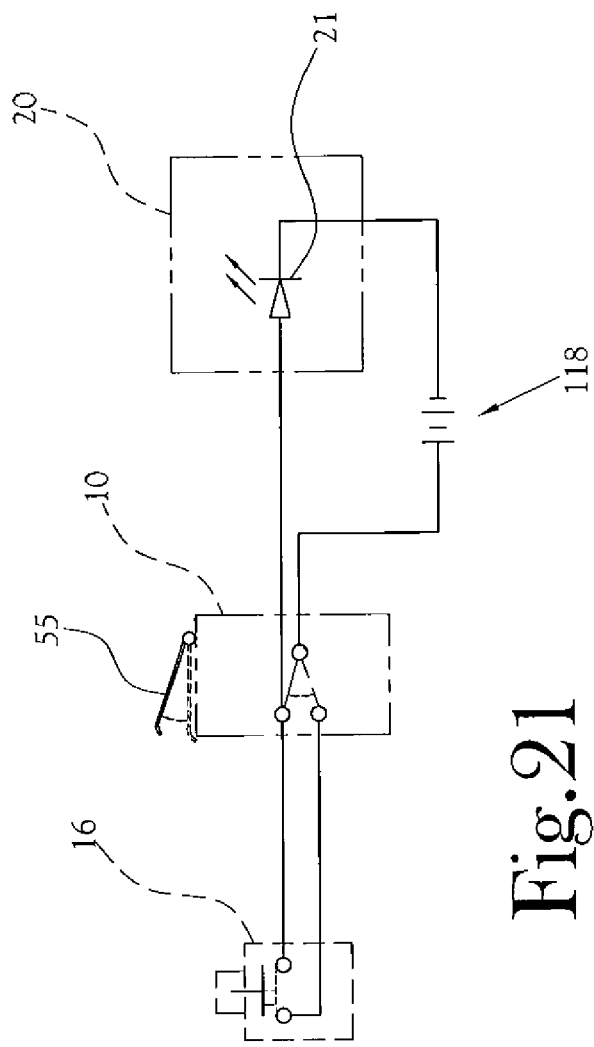

Within the hollow interior of the switch housing there is disposed a section of the call cord to which the housed switch is electrically incorporated. Referring to the diagrammatic electric circuit of FIG. 21, it will be noted that in the depicted embodiment, the electrical circuit with the incorporated call cord comprises a source of electrical power 118, an alert device 21 within the nurse's station, a push button-type switch 16 and a housed switch 10. As seen in FIG. 21, the push-button switch may comprise a normally open switch interposed within the electrical circuit. When this push-button switch is closed an electrical signal can pass to the alert device at the nurse's station.

The depicted housed switch includes a top surface 118 on which there is mounted a resilient lever 55 which is biased to position the distal outboard end 120 of the lever in spaced apart relationship relative to the top surface of the body member of the switch when the switch housing is disassociated from the bracket. As is known in the art, one end of the lever extends interiorly of the body member of the switch wherein such end of the lever is positioned to actuate the switch when the outboard end of the lever is urged toward the top end of the switch. In the embodiment depicted in FIG. 21, when the switch housing is disassociated from the bracket, the lever is biased away from the top end of the switch.

Figure 22:
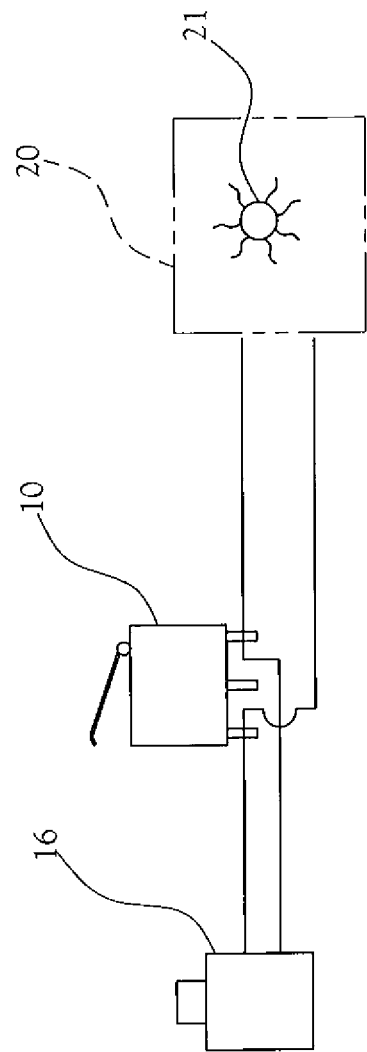
FIG. 22 is a schematic diagram depicting the functionality of the present invention.

FIG. 22 depicts diagrammatically the functioning of the present invention. Specifically, when the lever is in its down position such as when the housed switch is mounted within its bracket), that portion of the electrical circuit containing the push-button switch is open (ie., the push-button is electrically activatable for sending an alert signal to the nurse's station). Under these conditions the patient may use the push-button switch to send an alert signal to the nurse's station. In the present invention, when the lever is up, such as when the housed switch is disassociated from its bracket, that portion of the electrical circuit which includes the push-button switch is electrically isolated and the push-button switch is rendered inoperable for sending an alert signal to the nurse's station. However, under these latter conditions wherein the lever is up, the nurse's station is electrically activated and a continuous alert signal is being sent to the nurse's station.

Accordingly, by reason of the affixation of the call cord to the housed switch in the switch housing, actuation of the housed switch is a function of the presence or absence of the housed switch and that portion of the call cord associated with the housed switch in the bracket. Consequently, operative disassociation of the call cord and its accompanying housed switch from the mounting bracket may be accomplished only by deliberate physical withdrawal of the switch from the bracket.

From the foregoing, it will be recognized that if the housing of the spring switch is pulled apart from the bracket, the post 52 is withdrawn from engagement with the lever 55 so that the lever returns to its original up-biased state wherein the push-button switch is out of the electrical circuit and therefore inoperable for initiating alert signals which are received at the nurse's station. By this means, the patient can be precluded from undesirable repeated initiation of alert signals to the nurse's station by the care giver merely separating the housed switch from its bracket. As desired, means may be provided within the patient's room for the continuous alert signal being received at the nurse's station when the push-button switch has been deactivated.

The components of the present invention may be constructed of high impact molded plastic. The cord may comprise a flexible PVC jacketed cable, with an overall length dictated by the environmental circumstances. The push-button switch may be a conventional momentary-action push-button switch. The cord and molded assembly materials preferably permit cleaning with standard hospital cleaning agents.

While the present invention has been illustrated by description of various embodiments and while the illustrative embodiments have been described in considerable detail, it is not the intentions of the applicant to restrict or in any way limit the scope of the appended claims to such detail. Additional advantages and modifications will readily appear to those skilled in the art. For example, the electrical circuitry of the present invention may be varied in ways which will be recognized by one skilled in the art, such as by designing the electric circuit whereby the housed switch, and/or the push-button type switch may be incorporated into an electrical circuit in a manner which produces the same result as disclosed herein, but by means other than the depicted housed switch. The invention in its broader aspects is therefore not limited to specific details, representative apparatus and methods, and illustrative examples shown and described. Accordingly, departure may be made from such details without departing from the spirit or scope of applicant's general inventive concept.

What is claimed is:

1. A call cord adapted to initiate and transmit at least one alert signal from a first location to a remote second location comprising;
   an electrical conductor having opposite ends;
   a housed switch electrically and physically integrated with said electrical conductor at a location along the length of said electrical conductor intermediate said opposite ends,
   a non-electrically conductive housing physically encasing said housed switch and a portion of said electrical conductor therein,
   an operatively cooperative fixed mounting bracket adapted to releasably receive said housing therein,
   whereby actuation of said housed switch is a function of the association or disassociation of said housing and call cord relative to said fixed mounting bracket.

2. The call cord of claim 1 wherein said actuation of said housed switch may be accomplished only by physical association or disassociation of said housing relative to said bracket.

3. The call cord of claim 1 wherein said call cord includes a button-type switch incorporated in said call cord, said button-type switch be actuatable by a user of the call cord, and said housed switch comprises an actuation lever associated with said housed switch and biased toward a position wherein said button-type switch is operable for initiating and transmitting an alert signal to a location remote from said button-type switch.

4. The call cord of claim 3 wherein association of said actuation lever of said housed switch with said bracket actuates said housed switch to electrically remove said button-type switch from electrical communication and to initiate and transmit an alert signal to said location remote from said button-type switch for such time period as said actuation lever is associated with said housed switch.

5. The call cord of claim 4 wherein said housing includes an opening through the wall thereof at a location proximate said housed switch and post means associated with said bracket, said post means being in register with said opening and having a distal end thereof projecting into said switch housing when said switch housing is operatively engaged with said bracket, by a distance whereby said distal end of said post means physically engages and actuates said housed switch to deactivate said button-type switch so long as said housing is substantially fully mounted within said bracket.

6. The call cord of claim 5 wherein disengagement of said switch housing from said bracket effects at least partial withdrawal of said post means from said housing and said housed switch returns to its biased position.

7. The call cord of claim 1 wherein said bracket is adapted to be anchored to a substantially fixed structure proximate a potential user of said call cord.

8. The call cord of claim 1 wherein said bracket includes a manually operable latch adapted to releasably retain said housed swith within said bracket.

9. The call cord of claim 1 wherein said switch housing comprises a base and a cover defining a substantially hollow chamber therewithin adapted to receive therein at least a section of said call cord and said housed switch.

10. The call cord of claim 9 wherein said base and said cover are joined to one another employing mating multiple fasteners disposed about the perimeters of said base and cover, said fasteners being abnormally resistant to release from their mating engagement.

11. The call cord of claim 1 wherein said push-button type switch is adapted to initiate and transmit repeated independent alert signals to said remote location and said housed switch is adapted to initiate and transmit a single continuous alert signal to said remote location.

12. The call cord of claim 10 wherein said single continuous alert signal continues so long as said switch housing is disassociated from said bracket.

\* \* \* \* \*